United States Patent
Tachikawa et al.

[11] Patent Number: 5,986,124
[45] Date of Patent: Nov. 16, 1999

[54] METHOD FOR MAKING COMPOUNDS CONTAINING HYDROCARBONOXYSILYL GROUPS BY HYDROSILYLATION USING HYDRIDO (HYDROCARBONOXY) SILANE COMPOUNDS

[75] Inventors: Mamoru Tachikawa; Kasumi Takei, both of Kanagawa, Japan

[73] Assignee: Dow Corning Asia, Ltd., Tokyo, Japan

[21] Appl. No.: 09/218,533

[22] Filed: Dec. 21, 1998

[30] Foreign Application Priority Data

Dec. 24, 1995 [JP] Japan .................................. 9-355185

[51] Int. Cl.$^6$ ....................................................... C07F 7/08
[52] U.S. Cl. ................................................................ 556/479
[58] Field of Search ................................................ 516/479

[56] References Cited

U.S. PATENT DOCUMENTS

| | | | |
|---|---|---|---|
| 5,424,470 | 6/1995 | Bank et al. | 556/479 |
| 5,449,802 | 9/1995 | Bank et al. | 556/479 |
| 5,481,016 | 1/1996 | Bank et al. | 556/479 |
| 5,486,637 | 1/1996 | Bank et al. | 556/479 |
| 5,616,763 | 4/1997 | Bank et al. | 556/479 |

*Primary Examiner*—Paul F. Shaver
*Attorney, Agent, or Firm*—William F. Boley

[57] ABSTRACT

A method for preparing compounds containing (hydrocarbonoxy)silyl groups by reacting an unsaturated organic compound with a hydrido (hydrocarbonoxy)silane compounds by means of the catalytic action of platinum or a platinum compound in the presence of a carboxylic acid compound.

13 Claims, No Drawings

METHOD FOR MAKING COMPOUNDS CONTAINING HYDROCARBONOXYSILYL GROUPS BY HYDROSILYLATION USING HYDRIDO (HYDROCARBONOXY) SILANE COMPOUNDS

BACKGROUND OF INVENTION

The present invention is a method for manufacturing industrially important compounds containing (hydrocarbonoxy)silyl groups with good efficiency using hydrido (hydrocarbonoxy) silane compounds and aliphatic unsaturated organic compounds as source materials.

Hydrido (hydrocarbonoxy)silane compounds, as typified by SiH-functional alkoxysilanes, are important raw materials of modified silicones and are also used as crosslinking agents, for example, in the surface modification of various types of substrates and in curing reactions of polymers.

Methods for manufacturing compounds containing (hydrocarbonoxy)silyl groups, as typified by alkoxysilyl groups, can be divided into the following two main categories:

1. Methods in which a hydrosilylation reaction is caused to take place between aliphatic unsaturated organic compounds and hydridochlorosilane compounds, and in which an alcohol decomposition of the chlorine atoms bonded to the silicon atoms is further performed.
2. Methods in which a hydrosilylation reaction is caused to take place between aliphatic unsaturated organic compounds and hydridoalkoxysilane compounds.

Of these methods, the second method involve a simple process and allow the manufacture of products containing few ionic impurities. However, in order to perform the second method effectively, the use of a catalyst which has superior activity and selectivity for the hydrosilylation reaction is indispensable.

In regard to hydrosilylation reactions, it is known that certain types of compounds prevent a loss of activity by the catalyst and increase the reaction activity. However, such characteristics are limited to chlorosilane compounds and siloxane compounds. Furthermore, in the case of hydrosilylation reactions, it is often necessary to add oxygen to the reaction atmosphere in order to realize and maintain the catalytic activity and accordingly there is a danger of ignition and explosion.

The object of the present invention is to provide a novel method for making compounds containing (hydrocarbonoxy)silyl groups by means of a hydrosilylation reaction using hydrido (hydrocarbonoxy)silane compounds. Specifically, the present invention makes it possible to make compounds containing (hydrocarbonoxy)silyl groups by increasing the activity of the platinum or platinum compound catalyst in a hydrosilylation reaction between a hydrido (hydrocarbonoxy)silane compound and an aliphatic unsaturated organic compound, and preventing any drop in this activity so that hydrosilylation can be performed efficiently and economically.

Furthermore, the activity of the aforementioned platinum catalyst is increased, and the duration of this activity is improved, by the present method. As a result, the hydrosilylation reaction can be performed at a low oxygen partial pressure or in an inert atmosphere so that the danger of ignition or explosion during the hydrosilylation reaction is reduced.

SUMMARY OF INVENTION

The present invention is characterized by a hydrosilylation reaction using a platinum or platinum compound catalyst, the reaction activity of which is greatly improved by supplying a carboxylic acid compound to the method when a hydrido (hydrocarbonoxy)silane compound is reacted with an olefin-functional or acetylene-functional aliphatic unsaturated organic compound. The hydrosilylation reaction can be performed quickly at a low oxygen partial pressure or in the absence of oxygen.

DESCRIPTION OF INVENTION

The present invention is a method for manufacturing compounds containing (hydrocarbonoxy)silyl groups comprising reacting a hydrido (hydrocarbonoxy)silane compound described by formula $$HSiR_n(OR')_{3-n} \qquad (1)$$

with an aliphatic unsaturated organic compound in the presence of platinum or a compound of platinum catalyst and a carboxylic acid compound; where each R is a hydrocarbon group independently selected from the group consisting of (1) hydrocarbon groups comprising 1 to 10 carbon atoms and (2) hydrocarbon groups comprising 1 to 10 carbon atoms which have atoms selected from the group consisting of O, F, Cl, Br, I and Si; each R' is a hydrocarbon group independently selected from the group consisting of (3) hydrocarbon groups comprising 1 to 18 carbon atoms and (4) hydrocarbon groups comprising 1 to 18 carbon atoms which have atoms selected from the group consisting of O, F, Cl, Br, I and Si; and n=0, 1, or 2.

The hydrido(hydrocarbonoxy)silane compounds used in the present method are described by formula (1). These compounds are silicon compounds which have hydrogen atoms bonded directly to silicon atoms and which have at least one (hydrocarbonoxy) group described by OR' bonded to a silicon atom. Different (hydrocarbonoxy) groups may be bonded to the same silicon atom. In formula (1), R is a hydrocarbon group selected from the group consisting of (1) hydrocarbon groups comprising 1 to 10 carbon atoms and (2) hydrocarbon groups comprising 1 to 10 carbon atoms which also have atoms selected from the group consisting of O, F, Cl, Br, I, and Si; In formula (1), R' is a hydrocarbon group selected from the group consisting of (3) hydrocarbon groups comprising 1 to 18 carbon toms and (4) hydrocarbon groups comprising 1 to 18 carbon atoms which also have atoms selected from the group consisting of O, F, Cl, Br, I, and Si. R' is preferably a group comprising 1 to 10 carbon atoms in the abovementioned (3) or (4).

In regard to R, in cases where n=2, different hydrocarbon groups may be bonded to the same silicon atom. Among the abovementioned hydrocarbon groups, it is desirable that R and R' be alkyl groups, which may have atoms selected from the abovementioned group consisting of O, F, Cl, Br, I, and Si. Examples of substituent groups R include alkyl groups such as methyl, ethyl, n-propyl, isopropyl, n-butyl, t-butyl, pentyl, hexyl, octyl, and decyl; alkenyl groups such as 2-propenyl, hexenyl, and octenyl; aralkyl groups such as benzyl and phenethyl; aryl groups such as phenyl, tolyl, and xylyl; chloromethyl;, 4-chlorophenyl; trimethylsilylmethyl; and 2-

Examples of R' include the same groups as those cited for the abovementioned R.

The following compounds may be cited as examples of hydrido (hydrocarbonoxy)silane compounds: specifically, examples of trialkoxysilanes, trialkenoxysilanes and triaryloxysilanes include trimethoxysilane, triethoxysilane, tri-n-propoxysilane, triisopropoxysilane, tributoxysilane, triisopropenoxysilane, and triphenoxysilane. Examples of dialkoxysilanes, dialkenoxysilanes, and diaryloxysilanes include methyldimethoxysilane, methyldiethoxysilane, methyldi-n-propoxysilane, methydiisopropenoxysilane, methyldiphenoxysilane, ethyldimethoxysilane, ethyldiethoxysilane, n-propyldimethoxysilane, n-propyldiethoxysilane, 3,3,3-trifluoropropyldimethoxysilane, 3,3,3-trifluoropropyldiethoxysilane, n-hexyldimethoxysilane, n-hexyldiethoxysilane, n-octyldimethoxysilane, n-octyldiethoxysilane, benzyldimethoxysilane, benzyldiethoxysilane, phenethyldimethoxysilane, phenethyldiethoxysilane, phenyldimethoxysilane, and phenyldiethoxysilane. Examples of monoalkoxysilanes, monoalkenoxysilanes and monoaryloxysilanes include dimethylmethoxysilane, dimethylethoxysilane, dimethyl-n-propoxysilane, dimethylisopropenoxysilane, dimethylphenoxysilane, diethylmethoxysilane, methylethylethoxysilane, n-propyl(methyl)methoxysilane, n-propyl(methyl)ethoxysilane, 3,3,3-trifluoropropyl (methyl)methoxysilane, bis (3,3,3-trifluoropropyl) ethoxysilane, n-hexyl(methyl) methoxysilane, di(n-hexyl) ethoxysilane, n-octyl(methyl)methoxysilane, di(n-octyl) ethoxysilane, benzyl(methyl)methoxysilane, phenethyl (methyl)methoxysilane and methylphenylmethoxysilane. Examples of hydrido (hydrocarbonoxy)silane compounds with mixed alkoxy groups, alkenoxy groups, aralkyloxy groups, and aryloxy groups include diethoxypropenoxysilane, dimethoxyphenoxysilane, diphenoxypropenoxysilane, and methylmethoxyphenethoxysilane. Furthermore, compounds in which the R or R' of the abovementioned silane compounds are replaced by chloromethyl groups, 4-chlorophenyl groups, trimethylsilylmethyl groups, or 2-methoxyethyl groups may also be cited as examples.

These hydrido (hydrocarbonoxy)silane compounds are selected according to their reactivity or according to the application of the hydrido (hydrocarbonoxy)silyl-group-containing compound that is to be manufactured. Ordinarily, taking reactivity into account, alkoxysilanes are preferred for use.

It is preferred that the hydrido (hydrocarbonoxy)silane compound be a compound described by formula

$$HSiR_n(OR'')_{3-n} \qquad (2)$$

where each R and R" is a hydrocarbon group independently selected from the group consisting of (1) hydrocarbon groups comprising 1 to 10 carbon atoms and (2) hydrocarbon groups comprising 1 to 10 carbon atoms which also have atoms selected from the group consisting of O, F, Cl, Br, I and Si; and n=1 or 2.

Different hydrocarbonoxy groups may be bonded to the same silicon atom. In cases where one or two hydrocarbonoxy groups are bonded to such a silicon atom, the remaining substituent groups bonded to the silicon atom are hydrogen atoms or hydrocarbon groups expressed by R in formulas (1) and (2).

The term "aliphatic unsaturated organic compound" used in the present method refers to an aliphatic hydrocarbon group which has unsaturated groups. The aliphatic unsaturated organic compounds are selected from the group consisting of (1) olefinic unsaturated compounds, (2) olefinic unsaturated compounds which have atoms selected from the group consisting of O, N, F, Cl, Br, I, S, and Si; (3) acetylenic unsaturated compounds, and (4) acetylenic unsaturated compounds which have atoms selected from the group consisting of O, N, F, Cl, Br, I, S, and Si.

Specific examples of (1) olefinic unsaturated compounds include linear terminalunsaturated olefin compounds, such as ethylene, propylene, butene-1, hexene-1, octene-1 and octadecene-1; branched olefin compounds which have terminal unsaturated groups such as isobutylene, 3-methylbutene-1,3,5-dimethylbutene-1, and 4-ethyloctene-1; linear internal olefin compounds such as butene-2, hexene-3, octene-2, and octadecene-4; branched internal olefin compounds such as 2-methylbutene-2,3,5-dimethylhexene-2 and 4-ethyloctene-2; cyclic olefin compounds such as cyclopentene, cyclohexene, cyclooctene, and cyclodecene; olefin compounds containing aryl groups such as allylbenzene and 4-phenylbutene-1, and diene compounds such as 1,3-butadiene, 1,5-hexadiene, 1,3-octadiene, cyclopentadiene, 1,3-cyclohexadiene, and 1,5-cyclooctadiene.

Examples of (2) olefinic unsaturated compounds which contain atoms selected from a set consisting of oxygen, nitrogen, halogens (F, Cl, Br, I), silicon, and sulfur include oxygen-containing allyl compounds such as allylglycidyl ether and allyl methacrylate; amine compounds such as N-vinylcarbazole; olefin halides such as allyl chloride, 4-chlorobutene-1, and 6-bromohexene-1; silicon-functional olefin compounds such as vinyltrimethylsilane, 1,3-divinyl-1,1,3,3-tetramethyl-1,3-disiloxane, vinyltriethoxysilane, and allyloxytrimethylsilane; and sulfur-containing olefin compounds such as allylmercaptan and allyl sulfide.

Examples of (3) acetylenic unsaturated compounds include linear terminal-unsaturated acetylene compounds such as acetylene, propyne, butyne-1, and hexyne-1 and internal acetylene compounds such as butyne-2 and hexyne-3.

Examples of (4) acetylenic unsaturated compounds which contain at least one atom selected from the group consisting of oxygen, nitrogen, halogens (F, Cl, Br, I), silicon, and sulfur include acetyl alcohols such as 2-methyl-3-butyn-2-ol and propargyl alcohol; halogenated acetylene compounds such as 4-chlorobutyne-1; silicon-functional acetylene compounds such as trimethylsilylated propargyl alcohol; and sulfur-containing olefins such as propargylmercaptan and propargyl sulfide.

Furthermore, in cases where vinylsilane compounds are used as olefinic unsaturated compounds in the present invention, the reactivity and positional selectivity are improved by the presence of the carboxylic acid compound. The following compounds may be cited as examples of such vinylsilane compounds: vinyltrimethylsilane, vinyltriethylsilane, vinyldimethylphenylsilane, vinylethoxydimethylsilane, vinylmethoxydiethylsilane, vinylphenoxydimethylsilane, vinyldimethoxymethylsilane, vinyldiethoxymethylsilane, vinyldi (n-propoxy) methylsilane, vinyltrimethoxysilane, vinyltriethoxysilane, divinyldimethylsilane, divinylmethylphenylsilane and divinylethoxysilane. In the present method, a vinyl compound is a preferred aliphatic unsaturated organic compound.

In the present invention, the platinum compound catalyst may be selected from the group consisting of complexes with a minus charge, 0-valent, divalent or tetravalent platinum compounds and platinum colloids. Specifically, examples of complexes with a minus charge include platinum carbonyl cluster anion compounds such as $(Pt_3(CO)_6)^{2-}$, $(Pt_3(CO)_6)_2^{2-}$ and $(Pt_3(CO)_6)_4^{2-}$. Examples of 0-valent platinum compounds include platinum (0) divinyltetramethyldisiloxane complexes, platinum (0) tetravinyltetramethylcyclotetrasiloxane complexes, platinum (0) ethylene complexes, and platinum (0) styrene complexes. Examples of divalent platinum compounds include Pt(II) Cl$_2$, Pt(II)Br$_2$, bis (ethylene) Pt(II)Cl$_2$, (1,5-cyclooctadiene) Pt(II)Cl$_2$, platinum (II) acetylacetonate and bis (benzonitrile) Pt(II)

$Cl_2$. Examples of tetravalent platinum compounds include $Pt(IV)Cl_4$, $H_2Pt(IV)Cl_6$, $Na_2Pt(IV)Cl_6$, and $K_2Pt(IV)Cl_6$. Among these compounds, platinum (0) divinyltetramethyldisiloxane complexes and alcohol solutions of chloroplatinic acid may be cited as examples of especially desirable platinum compound catalysts from the standpoint of utility, such as solubility in organic solvents and stability of the catalyst solution. The amount of platinum required for the hydrosilylation reaction of a given amount of substrate varies according to factors such as the type of substrate, reaction temperature, and reaction time. Generally, such a catalyst can be used in the range of $10^{-3}$ moles to $10^{-8}$ moles of platinum per mole of hydrido (hydrocarbonoxy)silane compound. From the standpoints of catalyst economy and reaction time, a platinum concentration in the range of $10^{-4}$ moles to $10^{-7}$ moles is preferred.

The carboxylic acid compounds used in the present invention are compounds selected from the group consisting of (a), (b), (c) (d) described as follows:

(a) Carboxylic acids, with no particular restrictions on these acids, as long as the acids have carboxyl groups. Examples of such acids include saturated carboxylic acids, unsaturated carboxylic acids, monocarboxylic acids and dicarboxylic acids. The portions of these carboxylic acids other than the carboxyl groups are ordinarily selected from the group consisting of saturated or unsaturated aliphatic hydrocarbon groups, aromatic hydrocarbon groups, halogenated hydrocarbon groups and hydrogen atoms. Furthermore, substituent groups such as amino groups, silyl groups, or hydroxyl groups may also be bonded to these hydrocarbon groups.

(b) Carboxylic anhydrides.

(c) Silylated carboxylic acids.

(d) Compounds which generated carboxylic acid compounds of the abovementioned (a), (b), or (c) by decomposition or reaction in the method during the hydrosilylation reaction of the present invention.

In the present method it is necessary that the carboxylic acid compounds be present when the hydrosilylation reaction takes place. Accordingly, it is necessary to add such compounds to the method prior to the initiation of the hydrosilylation reaction or by the early stages of the reaction.

Carboxylic acids, silylated carboxylic acids, or carboxylic anhydrides are suitable as the carboxylic acid compounds used in the present method. In addition to these, however, compounds which generate the abovementioned carboxylic acid compounds by decomposition or a reaction in the method are also included. Specific examples of carboxylic acids include saturated monocarboxylic acids such as formic acid, acetic acid, propionic acid, n-butyric acid, isobutyric acid, hexanoic acid, cyclohexanoic acid, lauric acid, and stearic acid; saturated dicarboxylic acids such as oxalic acid and adipic acid; aromatic carboxylic acids such as benzoic acid and para-phthalic acid; carboxylic acids such as chloroacetic acid, dichloroacetic acid, trifluoroacetic acid, para-chlorobenzoic acid, and trimethylsilylacetic acid in which the hydrogen atoms of the hydrocarbon groups of the carboxylic acid are replaced by halogen atoms or organosilyl groups; unsaturated fatty acids such as acrylic acid, methacrylic acid, and oleic acid; and compounds which have hydroxy groups, carbonyl groups or amino groups in addition to carboxyl groups, for example, hydroxy acids such as lactic acid, keto acids such as acetoacetic acid, aldehyde acids such as glyoxylic acid, and amino acids such as glutamic acid. Specific examples of silylated carboxylic acids include trialkylsilylates of carboxylic acids such as trimethylsilyl formate, trimethylsilyl acetate, triethylsilyl propionate, trimethylsilyl benzoate, and trimethylsilyl trifluoroacetate; and di-, tri- and tetracarboxylates such as dimethyldiacetoxysilane, methyltriacetoxysilane, and silicon tetrabenzoate.

Examples of carboxylic anhydrides which can be used in the present method include acetic anhydride, propionic anhydride, and benzoic anhydride.

Examples of compounds which generate the abovementioned carboxylic acid compounds by decomposition or reactions in the present method include carboxylic acid halides such as acetyl chloride, butyryl chloride, and benzoyl chloride and metal salts of carboxylic acids.

These carboxylic acid compounds can be effectively used by being added to the present method at 0.001 Wt. % to 20 Wt. % of the reaction mixture; however, in order to achieve a sufficient effect and also use the compounds efficiently, it is desirable that such compounds be added at the rate of 0.01 Wt. % to 5 Wt. %. Here, the term "reaction mixture" refers to the mixture containing a hydrido (hydrocarbonoxy)silane compound, aliphatic unsaturated compound, catalyst consisting of platinum or a platinum compound, and the abovementioned carboxylic acid compound.

The reaction of the present method may be conducted at a temperature within a range of about 0° C. to 300° C.; however, a temperature of about 30° C. to 250° C. is optimal from the standpoints of achieving a suitable reaction rate and allowing the stable existence of the product and the substrates participating in the reaction.

In the present method the use of a solvent is not essential; however, hydrocarbon compounds, oxygen-containing organic solvents or silicones, for example, may be used as reaction solvents or solvents for the catalyst or in order to control the temperature of the method and facilitate the addition of the catalyst component. Examples of solvents which are optimal for such purposes include saturated or unsaturated hydrocarbon compounds such as hexane, cyclohexane, heptane, octane, dodecane, benzene, toluene, xylene, and dodecylbenzene and halogenated hydrocarbon compounds such as chloroform, methylene chloride, chlorobenzene, and ortho-dichlorobenzene; as well as ethers, esters, and silicones such as polydimethylsiloxanes with trimethylsilyl groups on both terminals and hexamethyldisiloxane.

Below, the present invention will be described in detail in terms of working examples; however, the present invention is not limited to these working examples. In the characterization of products in the examples given below GC-MS indicates gas chromatography—mass spectroscopy analysis. The conversion rate indicates the amount of the olefin raw material reacted, and the yield similarly indicates the amount of product produced relative to the amount of olefin raw material reacted.

The (hydrocarbonoxy)silane compounds, alkylsilane compounds, and siloxane compounds used in the present working examples were either commercially available compounds or compounds synthesized by generally known methods. The unsaturated compounds were commercially available compounds used "as is".

WORKING EXAMPLE 1

(Reaction of Octene-1 and Triethoxysilane by Means of a Platinum Catalyst in the Presence of Acetic Acid).

224 mg Of octene-1, 329 mg of triethoxysilane and 400 mg of toluene were placed in a glass reaction tube and 0.004 ml of acetic acid was then added to the tube. Then, 0.001 ml of a toluene solution of a 0-valent platinum complex of divinyltetramethyldisiloxane (platinum content: 0.4 wt %) was added to this mixture. The reaction tube was sealed with Teflon tape and heated for 30 minutes in an oil bath at 50° C. When the contents were analyzed by GC-MS following cooling, the conversion rate of the octene-1 was 96% and n-octyltriethoxysilane was produced at a yield of 89%.

Comparative Example 1
(Reaction of Octene-1 and Triethoxysilane by Means of a Platinum Catalyst in the Absence of a Carboxylic Acid Compound).

224 mg Of octene-1, 329 mg of triethoxysilane, and 400 mg of toluene were placed in a glass reaction tube. Next, 0.001 ml of a toluene solution of a 0-valent platinum complex of divinyltetramethyldisiloxane (platinum content: 0.4 wt %) was added to this mixture. The reaction tube was sealed with Teflon tape and heated for 30 minutes in an oil bath at 50° C. When the contents were analyzed by GC-MS following cooling, the conversion rate of octene-1 was 0.5% and n-octyltriethoxysilane was produced at a yield of 0.4%.

WORKING EXAMPLE 2
(Reaction of Octene-1 and Triethoxysilane by Means of a Platinum Catalyst in the Presence of Formic Acid).

224 mg Of octene-1, 328 mg of triethoxysilane and 56 mg of toluene were placed in a glass reaction tube and 0.002 ml of acetic acid was then added. Then, 0.001 ml of an isopropyl alcohol solution of chloroplatinic acid (platinum content: 0.39%) was added to this mixture. The reaction tube was sealed with Teflon tape and heated for 30 minutes in an oil bath at 50° C. When the contents were analyzed by GC-MS following cooling, the conversion rate of octene-1 was 96.6% and n-octyltriethoxysilane was produced at a yield of 92%.

Comparative Example 2
(Reaction of Octene-1 and Triethoxysilane by Means of a Platinum Catalyst in the Absence of a Carboxylic Acid Compound).

224 mg Of octene-1, 328 mg of triethoxysilane, and 56 mg of toluene were placed in a glass reaction tube. Next, 0.001 ml of a toluene solution of a 0-valent platinum complex of divinyltetramethyldisiloxane (platinum content: 0.4 wt %) was added to this mixture. The reaction tube was sealed with Teflon tape and heated for 30 minutes in an oil bath at 50° C. When the contents were analyzed by GC-MS following cooling, the conversion rate of octene-1 was 2.5% and n-octyltriethoxysilane was produced at a yield of 1.5%.

WORKING EXAMPLE 3
(Reaction of Octene-1 and Triethoxysilane by Means of a Platinum Catalyst in the Presence of Trifluoroacetic Acid).

224 mg Of octene-1, 328 mg of triethoxysilane and 56 mg of toluene were placed in a glass reaction tube and 0.002 ml of trifluoroacetic acid then added. Then, 0.001 ml of a toluene solution of a 0-valent platinum complex of divinyltetramethyldisiloxane (platinum content: 0.4 wt %) was added to this mixture. The reaction tube was sealed with Teflon tape and heated for 30 minutes in an oil bath at 50° C. When the contents were analyzed by GC-MS following cooling, the conversion rate of octene-1 was 95.2% and n-octyltriethoxysilane was produced at a yield of 87.4%.

WORKING EXAMPLE 4
(Reaction of Octene-1 and Triethoxysilane by Means of a Platinum Catalyst in the Presence of Benzoic Acid).

224 mg Of octene-1, 328 mg of triethoxysilane and 56 mg of toluene were placed in a glass reaction tube and 8 mg of benzoic acid added. Then, 0.001 ml of an isopropyl alcohol solution of chloroplatinic acid (platinum content: 0.39%) was added to this mixture. The reaction tube was sealed with Teflon tape and heated for 30 minutes in an oil bath at 50° C. When the contents were analyzed by GC-MS following cooling, the conversion rate of octene-1 was 97.5% and n-octyltriethoxysilane was produced at a yield of 91%.

WORKING EXAMPLE 5
(Reaction of Octene-1 and Triethoxysilane by Means of a Platinum Catalyst in the Presence of Methyltriacetoxysilane).

224 mg Of octene-1, 328 mg of triethoxysilane, and 56 mg of toluene were placed in a glass reaction tube and 4 mg of methyltriacetoxysilane were added. Then, 0.001 ml of a toluene solution of a 0-valent platinum complex of divinyltetramethylsiloxane (platinum content: 0.4 wt %) was added to this mixture. The reaction tube was sealed with Teflon tape and heated for 30 minutes in an oil bath at 50° C. When the contents were analyzed by GC-MS following cooling, the conversion rate of octene-1 was 97.6% and n-octyltriethoxysilane was produced at a yield of 91%.

WORKING EXAMPLE 6
(Reaction of Octene-1 and Triethoxysilane by Means of a Platinum Catalyst in the Presence of Acetic Anhydride).

224 mg Of octene-1, 328 mg of triethoxysilane, and 56 mg of toluene were placed in a glass reaction tube and 0.01 ml of acetic anhydride was added to this mixture. Then, 0.001 ml of a toluene solution of a 0-valent platinum complex of divinyltetramethyldisiloxane (platinum content: 0.4 wt %) was added to this mixture. The reaction tube was sealed with Teflon tape and heated for 30 minutes in an oil bath at 50° C. When the contents were analyzed by GC-MS following cooling, the conversion rate of octene-1 was 16.5%, and n-octyltriethoxysilane was produced at a yield of 14.3%.

WORKING EXAMPLE 7
(Reaction of Allyl Chloride and Methyldimethoxysilane by Means of a Platinum Catalyst in the Presence of Acetic Acid).

306 mg Of allyl chloride, 530 mol of dimethyldimethoxysilane, and 77 mg of toluene were placed in a glass reaction tube and 0.01 ml of acetic acid was added to this mixture. Then, 0.005 mol of a toluene solution of a 0-valent platinum complex of divinyltetramethyldisiloxane (platinum content: 0.4 wt %) was added to this mixture. The reaction tube was sealed and heated for 2 hours in an oil bath at 50° C. When the contents were analyzed by GC-MS following cooling, the conversion rate of allyl chloride was 100% and γ-chloropropylmethyldimethoxysilane was produced at a yield of 40%.

Comparative Example 3
(Reaction of Allyl Chloride and Methyldiethoxysilane by Means of a Platinum Catalyst in the Absence of a Carboxylic Acid Compound).

306 mg of allyl chloride, 530 mol of dimethyldiethoxysilane, and 77 mg of toluene were placed in a glass reaction tube. Then, 0.005 mol of a toluene solution of a 0-valent platinum complex of divinyltetramethyldisiloxane (platinum content: 0.4 wt %) was added to this mixture. The reaction tube was sealed and heated for 2 hours in an oil bath at 50° C. When the contents were analyzed by GC-MS following cooling, the conversion rate of allyl chloride was 100% and γ-chloropropylmethyldimethoxysilane was produced at a yield of 19.7%.

WORKING EXAMPLE 8
(Reaction of 1,3-Divinyl-1,1,3,3-Tetramethyl-1,3-Disiloxane and Trimethoxysilane by Means of a Platinum Catalyst in the Presence of Acetic Acid).

186 mg Of 1,3-divinyl-1,1,3,3-tetramethyl-1,3-disiloxane, 246 mg of trimethoxysilane, and 47 mg of toluene were placed in a glass reaction tube and 0.005 ml of acetic acid was added to this mixture. Then, 0.002 ml of a toluene solution of a 0-valent platinum complex of divinyltetramethyldisiloxane (platinum content: 0.4 wt %) was added to this mixture. The reaction tube was sealed with Teflon tape and heated for 30 minutes in an oil bath at 59° C. When the contents were analyzed by GC-MS following cooling, the conversion rate of 1,3-divinyl-1,1,3,3-tetramethyl-1,3-disiloxane was 100%; furthermore, 1-β-trimethoxysilylethyl-3-α-trimethoxysilylethyl-1,1,3,3-tetramethyl-1,3-disiloxane was produced at a yield of 3.8% and 1,3-di (β-trimethoxysilylethyl)-1,1,3,3-tetramethyl-1,3-disiloxane was produced at a yield of 89%.

Comparative Example 4
(Reaction of 1,3-Divinyl-1,1,3,3-Tetramethyl-1,3-Disiloxane and Trimethoxysilane by Means of a Platinum Catalyst in the Absence of Carboxylic Acid Compound).

186 mg Of 1,3-divinyl-1,1,3,3-tetramethyl-1,3-disiloxane, 246 mg of trimethoxysilane, and 47 mg of toluene were placed in a glass reaction tube and 0.002 ml of a toluene solution of a 0-valent platinum complex of divinyltetramethyldisiloxane (platinum content: 0.4 wt %) was added to this mixture. The reaction tube was sealed with Teflon tape and heated for 30 minutes in an oil bath at 59° C. When the contents were analyzed by GC-MS following cooling, the conversion rate of 1,3-divinyl-1,1,3,3-tetramethyl-1,3-disiloxane was 8.3%; furthermore, 1-α-trimethoxysilylethyl-3-vinyl-1,1,3,3-tetramethyl-1,3-disiloxane was produced at a yield of 1.3%, 1-β-trimethoxysilylethyl-3-vinyl-1,1,3,3-tetramethyl-1,3-disiloxane was produced at a yield of 5.6%, and 1,3-di (β-trimethoxysilylethyl)-1,1,3,3-tetramethyl-1,3-disiloxane was produced at a yield of 1.7%.

WORKING EXAMPLE 9
(Reaction of Divinyldimethylsilane and Trimethoxysilane by Means of a Chloroplatinic Acid Catalyst in the Presence of Ethyltriacetoxysilane).

225 mg Of divinyldimethylsilane, 490 mg of trimethoxysilane, and 56 mg of toluene were placed in a glass reaction tube and 5 mg of ethyltriacetoxysilane was added to this mixture. This mixture was degassed and the reaction tube purged with nitrogen. Afterward, 0.5 microliters of an ethyl alcohol solution of chloroplatinic acid (platinum content: 3.77 wt %) was added. The reaction tube was sealed with Teflon tape and a rubber septum and was heated for 2 hours in an oil bath at 60° C. When the contents were analyzed by GC-MS following cooling, all of the vinyl groups had been consumed; and α,α-adducts were produced at the rate of 0.4%, α,β-adducts were produced at the rate of 12.5%, and β,β-adducts were produced at the rate of 87.1%. This corresponds to an α/β ratio of 1/14.

Comparative Example 5
(Reaction of Divinyldimethylsilane and Trimethoxysilane by Means of a Chloroplatinic Acid Catalyst in the Absence of a Carboxylic Acid Compound).

225 mg Of divinyldimethylsilane, 490 mg of trimethoxysilane, and 56 mg of toluene were placed in a glass reaction tube. This mixture was degassed and reaction tube purged with nitrogen. Afterward, 0.5 microliters of an ethyl alcohol solution of chloroplatinic acid (platinum content: 3.77 wt %) was added. The reaction tube was sealed with Teflon tape and a rubber septum and heated for 2 hours in an oil bath at 60° C. When the contents were analyzed by GC-MS, it was found that 1:1 adducts (α- and β-isomers) and 1:2 adducts (α,α-, α,β- and β,β-isomers) had been produced. The conversion rate of trimethoxysilane was 31% and 56% of the divinyldimethylsilane had been consumed. The α/β ratio of the hydrosilylation reaction was ½.

WORKING EXAMPLE 10
(Reaction of Vinyldimethylmethoxysilane and Trimethoxysilane by Means of a Platinum Catalyst in the Presence of Acetic Acid).

232 mg Of vinyldimethylmethoxysilane, 293 mg of trimethoxysilane (20% excess relative to the vinyl groups), and 60 mg of toluene were placed in a glass reaction tube and 5 mg of acetic acid was added to this mixture. This mixture was degassed and the reaction tube purged with nitrogen. Afterward, 5 microliters of a toluene solution of a 0-valent platinum complex of divinyltetramethyldisiloxane (platinum content: 0.4 wt %) was added to this mixture. The reaction tube was sealed with Teflon tape and heated for 2 hours in an oil bath at 60° C. When the contents were analyzed by GC-MS following cooling, it was found that the vinyldimethylmethoxysilane had been completely consumed and that the production ratio of α-adducts to β-adducts was 1:13.

Comparative Example 6
(Reaction of Vinyldimethylmethoxysilane and Trimethoxysilane by Means of a Platinum Catalyst in the Absence of a Carboxylic Acid Compound).

232 mg Of vinyldimethylmethoxysilane, 293 mg of trimethoxysilane (20% excess relative to the vinyl groups), and 60 mg of toluene were placed in a glass reaction tube. This mixture was degassed and the reaction tube purged with nitrogen. Afterward, 5 microliters of a toluene solution of a 0-valent platinum complex of divinyltetramethyldisiloxane (platinum content: 0.4 wt %) was added to this mixture. The reaction tube was sealed with Teflon tape and heated for 2 hours in an oil bath at 60° C. When the contents were analyzed by GC-MS following cooling, it was found that the vinyldimethylmethoxysilane had been completely consumed and that the production ratio of α-adducts to β-adducts was 1:3.

WORKING EXAMPLE 11
(Reaction of Allyl Glycidyl Ether (AGE) and Triethoxysilane by Means of a Platinum Catalyst in the Presence of Acetic Acid).

400 mg Of AGE, 457 mg of triethoxysilane, and 0.005 ml of acetic acid where added to a glass tube. Then, 0.005 ml of an isopropyl alcohol (IPA)/toluene solution of a 0-valent platinum complex of divinyltetramethyldisiloxane (platinum content: 0.02 Wt. %) was added to the tube and the tube sealed. The tube was heated in an oil bath at 100° C. for 1 hour. After cooling, the contents of the tube were analyzed by GC-MS and the AGE conversion was determined to be 91%, with a 0.06% yield of (2-glycidoxy)(1-methyl)ethyltriethoxysilane (beta-isomer) and 65% yield of 3-glycidoxypropyltriethoxysilane (gamma-isomer). The ratio of the beta-isomer to the gamma-isomer was 1:1083.

WORKING EXAMPLE 12
(Reaction of AGE and Triethoxysilane by Means of a Platinum Catalyst in the Presence of Lauric Acid).

400 mg Of AGE, 475 mg of triethoxysilane, and 26.6 mg of lauric acid were added to a glass tube. Then, 0.005 ml of an IPA/toluene solution of a 0-valent platinum complex of divinyltetramethyldisiloxane (platinum content: 0.02 Wt. %) was added to the tube and the tube sealed. The tube was heated in an oil bath at 100° C. for 1 hour. After cooling, the contents of the tube were analyzed by GC-MS and the AGE conversion was determined to be 96%, with a 0.06% yield of (2-glycidoxy)(1-methyl)ethyltriethoxysilane (beta-isomer) and 72% yield of 3-glycidoxypropyltriethoxysilane (gamma-isomer). The ratio of the beta-isomer to the gamma-isomer was 1:1200.

Comparative Example 7
(Reaction of AGE and Triethoxysilane by Means of a Platinum Catalyst in the Absence of a Carboxylic Acid Compound).

400 mg Of AGE and 475 mg of triethoxysilane were added to a glass tube. Then, 0.005 ml of an IPA/toluene solution of a 0-valent platinum complex of divinyltetramethyldisiloxane was added to the tube and the tube sealed. The tube was heated in an oil bath at 100° C. for 1 hour. After cooling, the contents of the tube were analyzed by GC-MS and the AGE conversion determined to be 54%, with a 0.5% yield of (2-glycidoxy)(1-methyl) ethyltriethoxysilane (beta-isomer) and 42% yield of 3-glycidoxypropyltriethoxysilane (gamma-isomer). The ratio of the beta-isomer to the gamma-isomer was 1:84.

WORKING EXAMPLE 13
(Reaction of AGE and Methyldimethoxysilane by Means of a Platinum Catalyst in the Presence of Acetic Acid).

494 mg Of AGE, 460 mg of methyldimethoxysilane, and 0.01 ml of acetic acid were added to a glass tube. Then, 0.006 ml of an IPA/toluene solution of a 0-valent platinum complex of divinyltetramethyldisiloxane (platinum content: 0.02 Wt. %) was added to the tube and the tube sealed. The tube was heated in an oil bath at 100° C. for 0.5 hour. After cooling, the contents of the tube were analyzed by GCMS and the AGE conversion was determined to be 89%, with a 0.05% yield of (2-glycidoxy)(1-methyl)ethyl(methyl) dimethoxysilane (beta-isomer) and 67% yield of 3-glycidoxypropyl(methyl)dimethoxysilane (gamma-isomer). The ratio of the beta-isomer to the gamma-isomer was 1:1340.

Comparative Example 8
(Reaction of AGE and Methyldimethoxysilane by Means of a Platinum Catalyst in the Absence of Carboxylic Acid Compound).

494 mg Of AGE and 460 mg of methyldimethoxysilane were added to a glass tube. Then, 0.006 ml of an IPA/toluene solution of a 0-valent platinum complex of divinyltetramethyldisiloxane (platinum content: 0.02 Wt. %) was added to the tube and the tube sealed. The tube was heated in an oil bath at 100° C. for 0.5 hour. After cooling, the contents of the tube were analyzed by GC-MS and the AGE conversion was determined to be 62%, with a 0.4% yield of (2-glycidoxy)(1-methyl)ethyl(methyl)dimethoxysilane (beta-isomer) and 48% yield of 3-glycidoxypropyl(methyl) dimethoxysilane (gamma-isomer). The ratio of the beta-isomer to the gamma-isomer was 1:140.

WORKING EXAMPLE 14
(Reaction of AGE with Methyldiethoxysilane by Means of a Platinum Catalyst in the Presence of Acetic Acid).

425 mg Of AGE, 500 mg of methyldiethoxysilane, and 0.01 ml of acetic acid were added to a glass tube. Then, 0.006 ml of an IPA/toluene solution of a 0-valent platinum complex of divinyltetramethyldisiloxane (platinum content: 0.02 Wt. %) was added to the tube and the tube sealed. The tube was heated in an oil bath at 100° C. for 0.5 hour. After cooling, the content of the tube was analyzed by GC-MS and the AGE conversion was determined to be 90%, with a 0.08% yield of (2-glycidoxy)(1-methyl)ethyl(methyl) diethoxysilane (beta-isomer) and 61% yield of 3-glycidoxypropyl(methyl)diethoxysilane (gamma-isomer). The ratio of the beta-isomer to the gamma-isomer was 1:870.

Comparative Example 9
(Reaction of AGE with Methyldiethoxysilane by Means of a Platinum Catalyst in the Absence of a Carboxylic Acid Compound).

425 mg Of AGE and 500 mg of methyldiethoxysilane were added to a glass tube. Then, 0.006 ml of an IPA/toluene solution of a 0-valent platinum complex of divinyltetramethyldisiloxane (platinum content: 0.02 Wt. %) was added to the tube and the tube sealed. The tube was heated in an oil bath at 100° C. for 0.5 hour. After cooling, the contents of the tube were analyzed by GC-MS and the AGE conversion was determined to be 26%, with a 0.5% yield of (2-glycidoxy)(1-methyl)ethyl(methyl)diethoxysilane (beta-isomer) and 20% yield of 3-glycidoxypropyl(methyl) diethoxysilane (gamma-isomer). The ratio of the beta-isomer to the gamma-isomer was 1:40.

WORKING EXAMPLE 15
(Reaction of AGE and Trimethoxysilane by Means of a Platinum Catalyst in the Presence of Ethyltriacetoxysilane).

320 mg Of AGE, 340 mg of trimethoxysilane, and 0.005 ml of ethyltriacetoxysilane were added to a glass tube. Then, 0.004 ml of an IPA/toluene solution of a 0-valent platinum complex of divinyltetramethyldisiloxane (platinum content: 0.02 Wt. %) was added to the tube and the tube heated in an oil bath at 100° C. for 0.5 hour. After cooling, the contents of the tube were analyzed by GC-MS and the AGE conversion was determined to be 86%, with a 0.08% yield of (2-glycidoxy)(1-methyl)ethyltrimethoxysilane (beta-isomer) and 71% yield of 3-glycidoxypropyl(acetoxy) dimethoxysilane (gamma-isomer). The ratio of the beta-isomer to the gamma-isomer was 1:888. The mixture also contained 1.4% of 3-glycidoxypropyl(acetoxy) dimethoxysilane. Addition of 0.05 ml of methanol to this mixture followed by stirring at room temperature converted this 3-glycidoxypropyl(acetoxy)dimethoxysilane to 3-glycidoxypropyltrimethoxysilane.

Comparative Example 10
(Reaction of AGE and Trimethoxysilane by Means of a Platinum Catalyst in the Absence of a Carboxylic Acid Compound).

320 mg Of AGE and 340 mg of trimethoxysilane were added to a glass tube. Then, 0.004 ml of an IPA/toluene solution of a 0-valent platinum complex of divinyltetramethyldisiloxane (platinum content: 0.02 Wt. %) was added to the tube and the tube heated in an oil bath at 100° C. for 0.5 hour. After cooling, the contents of the tube were analyzed by GC-MS and the AGE conversion was determined to be 47%, with a 0.4% yield of (2-glycidoxy)(1-methyl) ethyltrimethoxysilane (beta-isomer) and 39% yield of 3-glycidoxypropyl(acetoxy)dimethoxysilane (gamma-isomer). The ratio of the betaisomer to the gamma-isomer was 1:98.

We claim:

1. A method for making compounds containing (hydrocarbonoxy)silyl groups comprising reacting a hydrido (hydrocarbonoxy)silane compound described by formula

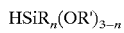

with an aliphatic unsaturated organic compound in the presence of a platinum or a compound of platinum catalyst and a carboxylic acid compound, where each R is a hydrocarbon group independently selected from the group consisting of hydrocarbon groups comprising 1 to 10 carbon atoms and hydrocarbon groups comprising 1 to 10 carbon atoms which have atoms selected from the group consisting of O, F, Cl, Br, I and Si; each R' is a hydrocarbon group independently selected from the group consisting of hydrocarbon groups comprising 1 to 18 carbon atoms and hydrocarbon groups comprising 1 to 18 carbon atoms which have atoms selected from the group consisting of O, F, Cl, Br, I and Si; and n=0, 1, or 2.

2. The method of claim 1, where the carboxylic acid compound is selected from the group consisting of carboxylic acids, silylated carboxylic acids, and carboxylic anhydrides.

3. The method of claim 2, where the carboxylic acid compound is present at a concentration of 0.001 to 20 weight percent of the total weight of components present in the method.

4. The method of claim 1, where the carboxylic acid compound is present at a concentration of 0.001 to 20 weight percent of the total weight of components present in the method.

5. The method of claim 1, where the hydrido (hydrocarbonoxy)silane is an alkoxysilane.

6. The method of claim 1, where each R and R' is a hydrocarbon group independently selected from the group consisting of hydrocarbon groups comprising 1 to 10 carbons atoms and hydrocarbon groups comprising 1 to 10 carbon atoms which also have atoms selected from the group consisting of O, F, Cl, Br, I, and Si; and n=1 or 2.

7. The method of claim 1, where the aliphatic unsaturated organic compound is a vinyl containing compound.

8. The method of claim 1, where the platinum compound catalyst is selected from the group consisting of platinum (0) divinyltetramethyldisiloxane complex and alcoholic solutions of chloroplatinic acid.

9. The method of claim 1, where the carboxylic acid compound is 0.01 to 5 weight percent of the total weight of components in the method.

10. The method of claim 1, where the reacting of the hydrido (hydrocarbonoxy)silane compound with the aliphatic unsaturated organic compound is conducted at a temperature within a range of about 0° C. to 300° C.

11. The method of claim 1, where the reacting of the hydrido (hydrocarbonoxy)silane compound with the aliphatic unsaturated organic compound is conducted at a temperature within a range of about 30° C. to 250° C.

12. The method of claim 1, where the aliphatic unsaturated organic compound is allyl glycidyl ether.

13. The method of claim 1, where the aliphatic unsaturated organic compound is allyl glycidyl ether and the hydrido (hydrocarbonoxy)silane is an alkoxysilane.

* * * * *